United States Patent
Hebecker et al.

(10) Patent No.: US 6,912,265 B2
(45) Date of Patent: Jun. 28, 2005

(54) METHOD FOR INTRAOPERATIVE GENERATION OF AN UPDATED VOLUME DATA SET

(75) Inventors: Axel Hebecker, Spardorf (DE); Matthias Mitschke, Nuremberg (DE); Norbert Rahn, Forchheim (DE); Dieter Ritter, Fuerth (DE)

(73) Assignee: Siemens Aktiengesellschaft, München (DE)

( * ) Notice: Subject to any disclaimer, the term of this patent is extended or adjusted under 35 U.S.C. 154(b) by 0 days.

(21) Appl. No.: 10/675,297

(22) Filed: Sep. 30, 2003

(65) Prior Publication Data

US 2004/0120469 A1 Jun. 24, 2004

(30) Foreign Application Priority Data

Sep. 30, 2002 (DE) .......................... 102 45 669

(51) Int. Cl.[7] .............................. A61B 6/03
(52) U.S. Cl. .................. 378/4; 378/8; 378/15; 378/901
(58) Field of Search ............. 378/4, 8, 15, 19, 378/901

(56) References Cited

U.S. PATENT DOCUMENTS 6,028,907 A * 2/2000 Adler et al. .................. 378/4
6,144,759 A 11/2000 Weese et al.
6,195,445 B1 * 2/2001 Dubuisson-Jolly et al. . 382/107
2004/0161144 A1 * 8/2004 Barth .......................... 382/154

FOREIGN PATENT DOCUMENTS

DE 198 07 884 9/1999

* cited by examiner

*Primary Examiner*—David V Bruce
(74) *Attorney, Agent, or Firm*—Schiff Hardin LLP (57) ABSTRACT

To intraoperatively generate an updated volume data set in which a image information of biological tissue is volume data set representing reconstructed from a series of n 2D biological tissue x-ray projections, one version, in intraoperatively acquired m 2D biological tissue x-ray projections the biological tissue 2D contour is segmented and this is back-projected in the reconstructed volume data set. In another version, in the volume data set the biological tissue 3D contour is segmented and this is projected in intraoperatively acquired m biological tissue 2D x-ray projections. The 3D contour is visually repositioned by projection in the m 2D x-ray projections in the volume data set, until its projection is substantially congruent with the biological tissue image information in the respective 2D x-ray projections. In both versions, a volume data set updated around the intraoperatively determined biological tissue 3D contour is generated.

22 Claims, 4 Drawing Sheets

METHOD FOR INTRAOPERATIVE
GENERATION OF AN UPDATED VOLUME
DATA SET

BACKGROUND OF THE INVENTION

1. Field of the Invention

The invention concerns methods for intraoperative generation of an updated volume data set of a patient.

2. Description of the Prior Art

In the course of a medical procedure on a patient, in particular a minimally invasive procedure, it is frequently necessary to monitor position changes of biological tissue in the patient by means of diagnostic x-ray imaging. Such a requirement exists, for example, in the case of complicated fractures, in particular multiple fractures with a number of small bone fragments with complex morphology, which in the osteosynthesis must be aligned and set relative to one another. Conventionally, the repositioning of the bone fragments and their subsequent setting ensue using individual 2D x-ray projections, and the surgeon during the minimally invasive procedure must mentally reconstruct the three-dimensional anatomical situation in reality from the 2D x-ray projections acquired at different viewing angles. This mental 3D reconstruction of the real three-dimensional anatomical situation from a number of 2D x-ray projections acquired intraoperatively requires a great deal of experience, imagination, and concentration on the part of the surgeon.

It also is possible to generate, with a C-arm x-ray device, a volume data set containing image information about the bone fragments at definite points in time after the positioning of the patient. To produce the volume data set a series of 2D x-ray projections is acquired at various projection angles. The surgeon would prefer to undertake the osteosynthesis using such volume data generated intraoperatively, from which 2D or 3D images can be generated. This is not currently possible because the 3D image data do not represent an image that is sufficiently current, since a frequent or even continuous complete intraoperative update of the 3D image data during the continuous repositioning of the bone fragments is not possible, both due to time consideration and due to radiation shielding consideration.

SUMMARY OF THE INVENTION

An object of the present invention is to provide a method to intraoperatively generate an updated volume data set with the least possible radiation exposure for the patient.

According to the invention, this object is achieved in a method according to the invention wherein, before a medical procedure on a patient, but after his or her positioning on a positioning device, a series of n 2D x-ray projections of biological tissue of the patient is acquired with an x-ray system at n different projection angles, from which image information is reconstructed from the volume data set using known projection geometries, for example in an offline calibration process or online during the patient measurement. This image information about the biological tissue represented in the volume data set is segmented, such that the 3D contour of the biological tissue is indicated in the volume data set. During the medical procedure, after a position change of the biological tissue, m<n 2D x-ray projections of the biological tissue of the patient are acquired with the x-ray system at m different projection angles, and their projection geometries are determined. The image information of the biological tissue is segmented in these intraoperatively acquired m 2D x-ray projections, such that the 2D contour of the biological tissue is indicated in each of the m 2D x-ray projections. Based on the determined projection geometries, the 2D contours of the biological tissue segmented in the 2D x-ray projections are back-projected in the reconstructed volume data set, such that a 3D contour of the biological tissue before and after its position change is present in each of the resulting and updated volume data sets. The 3D contour of the biological tissue changed with regard to its position in the updated volume data set can also be designated as a "pseudo 3D contour" of the biological tissue means an incompletely resolved 3D structure that is generated by the 2D -3D back-projection from some few 2D contours determined intraoperatively. However, this pseudo 3D contour is sufficient to visualize position and orientation of the biological tissue in its changed position. The method thus enables a volume data set of the patient containing current image information of biological tissue in its changed position to be generated during a medical procedure on a patient after acquisition of some few 2D x-ray projections, and thus with a significantly lower x-ray dose, compared to the case of a new acquisition of an entire series of n 2D x-ray projections, and in a clearly shorter amount of time in comparison to a new acquisition of an entire series of n 2D x-ray projections. Due to the smaller x-ray exposure for the patient and the comparatively shorter computing time, such an update of a volume data set can be undertaken repeatedly during a medical procedure.

In order to be able to better differentiate the 3D contour of the biological tissue in its initial position and the 3D contour of the biological tissue after its position change from one another, in an embodiment of the invention the 3D contour of the biological tissue in its initial position and the 3D contour of the biological tissue after its position change are displayed with respectively different visual appearances (i.e. they are differently "coded") to differentiate them from one another in the updated volume data set. According to an embodiment of the invention, the coding preferably is a greyscale or color coding, such that in the updated volume data set the 3D contour of the biological tissue in its original position and orientation is, for example, coded gray, and the 3D contour of the biological tissue in its updated position and orientation during the procedure is color coded.

In a further embodiment of the invention, the biological tissue if a bone fragment, or more usually a number of bone fragments which must be aligned and set relative to one another in the framework of an osteosynthesis.

In an embodiment of the invention, in an intraoperative acquisition of one of the m 2D x-ray projections, the x-ray system occupies a position relative to the patient that is substantially the same as in the acquisition of one of the 2D x-ray projections of the series of n 2D x-ray projections. This has the advantage that the projection geometries for this intraoperatively acquired 2D x-ray projection correspond to the projection geometries of the corresponding 2D x-ray projection of the series of n 2D x-ray projections, and are subsequently already prepared such that this can immediately be used to back-project the 2D contour of the biological tissue in the reconstructed volume data set. According to variants of this embodiment of the invention, the x-ray system can be caused to occupy the aforementioned position by the x-ray system being automatically adjusted by motor or manually into such a position under supervision of angle or position transmitters, or using a mechanical arresting device.

Alternatively, the x-ray system in an intraoperative acquisition of one of the m 2D x-ray projections can occupy another position relative to the patient, as in the acquisition of a 2D x-ray projection of the series of n 2D x-ray projections. In this case, the projection geometries for this position of the x-ray system must either be determined in a separate calibration process before the patient measurement or calculated by means of interpolation from the known or determined projection geometries of the x-ray system. Also in this case, the projection geometries are finally known in order to be able to back-project 2D contours of the biological tissue, that are segmented in the intraoperatively acquired m 2D x-ray projections, into the volume data set.

In a preferred embodiment of the invention, the x-ray system has a C-arm provided with an x-ray source and an x-ray radiation receiver. The C-arm preferably is isocentrically adjustable and is a component of a movable C-arm x-ray device.

The aforementioned object of the present invention also is achieved by a method wherein a volume data set containing image information about biological tissue is reconstructed from a series of 2D x-ray projections of a biological tissue of a patient after his or her positioning, the series being acquired with an x-ray system at n different projection angles using known projection geometries, for example from an offline calibration process. The image information of the biological tissue represented in the volume data set is segmented such that the 3D contour of the biological tissue is represented in the volume data set. During the medical procedure, m<n 2D x-ray projections of the biological tissue of the patient are acquired with the x-ray system at m different projection angles, and their projection geometries are determined. The 3D contour of the biological tissue segmented in the volume data set is subsequently projected in each of the m 2D x-ray projections and virtually repositioned in the volume data set until the 3D contour (preferably projected as a 2D contour in each of the m 2D x-ray projections) is substantially congruent with the image information of the biological tissue in the respective 2D x-ray projections. As a rule, this procedure proceeds iteratively. If congruity is achieved, the volume data set based on the information from the repositioning is updated around the 3D contour illustrating the position change of the biological tissue. Also with this method, based on an intraoperative acquisition of m 2D x-ray projections, an updated volume data set can be generated which contains both image information of the biological tissue of the patient in its initial position and updated image information of the biological tissue acquired during the implementation of a medical procedure, such that (for example, for a surgeon conducting the medical procedure) the difference between updated situation and initial position can be recognized in the volume data set.

In a further embodiment of the invention, the 3D contour is rotated and/or translationally adjusted until substantial congruity is achieved, according to a congruity criterion, between the 3D contour projected in the respective 2D x-ray projection and the image information of the biological tissue in the 2D x-ray projection. The congruity criterion can be that all corresponding points of corresponding 2D contours exhibit at least one predetermined distance from one another.

In order to be able to better differentiate the biological tissue in its initial position and the 3D contour of the biological tissue after its position change, in an embodiment of the inventive method, the 3D contour of the biological tissue on its initial position and the 3D contour of the biological tissue after its position change are shown coded in the updated volume data set. According to an embodiment of the invention, the coding here is a greyscale or color coding.

As was already explained, the biological tissue can be a bone fragment, or a number of bone fragments. Furthermore, according to variants of the invention, the x-ray system in an intraoperative acquisition of one of the m 2D x-ray projections can occupy a position relative to the patient that is substantially the same as in the acquisition of a 2D x-ray projection of the series of n 2D x-ray projections. In the acquisition of the m 2D x-ray projections, the x-ray system alternatively can occupy completely different positions, such that the projection geometries for these positions of the x-ray system must be determined in a calibration process or calculated by means of interpolation from known projection geometries.

According to a variant of the invention, the x-ray system (as described before) has a C-arm, provided with an x-ray source and an x-ray radiation receiver, which preferably is isocentrically adjustable and is a component (mobile) of a portable C-arm x-ray device.

DESCRIPTION OF THE PREFERRED EMBODIMENTS

Figure 1:
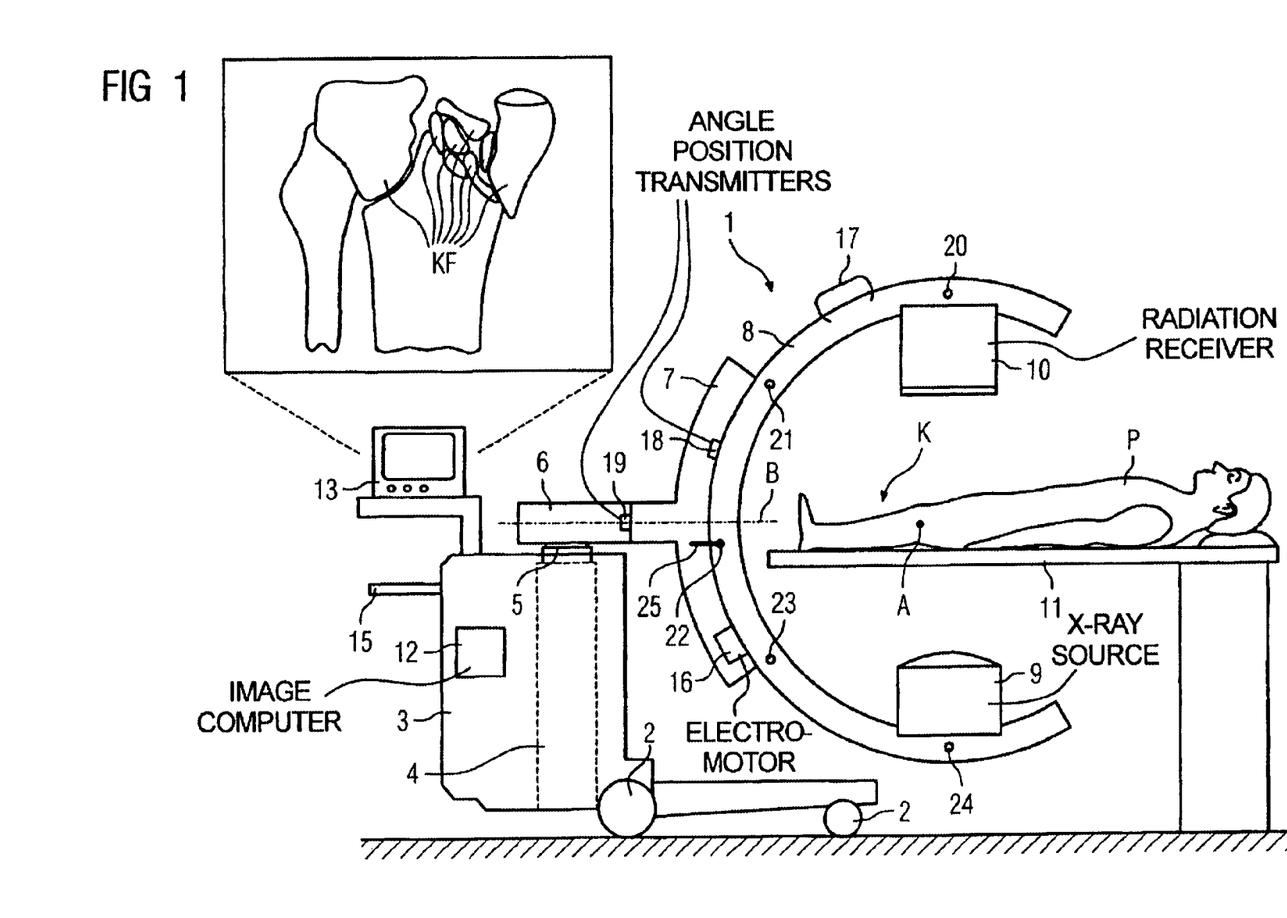
FIG. 1 shows a C-arm x-ray device to implement the inventive method.

The C-arm x-ray device 1 shown in FIG. 1 is suitable for implementing the inventive method and has a device cart 3, provided with wheels, in which is arranged a lifting device 4 (shown only schematically in FIG. 1) having a column 5. A holder 6 is arranged at the column 5 at which a positioner 7 is present to position a C-arm 8. An x-ray source 9 and an x-ray radiation receiver 10 are arranged opposite one another on the C-arm 8. The x-ray source 9 preferably emits a conical x-ray beam in the direction of the x-ray radiation receiver 10 (having a planar receiver surface), which can, for example, be an x-ray intensifier or a flat image detector. In the exemplary embodiment, the C-arm 8 can be isocentrically adjusted both around its orbital axis A (schematically indicated in the FIG. 1) and around its angulation axis B (schematically indicated in the FIG. 1).

Volume data sets, for example voxel volumes, can be generated with the C-arm x-ray device 1 representing body parts of a patient P positioned on a patient bed 11. In the exemplary embodiment, an image computer 12 is connected (in a manner not shown) in the cart 3 with the x-ray radiation receiver 10. The image computer 12 can reconstruct a volume data set or voxel volume of the body part to be imaged, by back-projection in a known manner from a series of n 2D x-ray projections, are acquired by moving the C-arm 8 around a body part of the patient P to be shown in an image) while irradiating the body part with the x-ray source 9 and detecting the attenuated radiation with the x-ray radiation receiver 10. The C-arm 8 is either adjusted along its perimeter around the orbital axis A or adjusted around the angulation axis B through approximately 190°. During the movement approximately 50 to 200 2D x-ray projections are acquired. The projection geometries necessary for the reconstruction of a voxel volume were determined in a known manner using a calibration phantom in an offline calibration of the C-arm x-ray device 1, and stored in a memory (not shown) of the C-arm x-ray device 1, to which the image computer 12 has access. An offline calibration to determine the projection geometries can ensue, for example, with a calibration phantom as described in German OS 100 47 382 having x-ray positive marks.

Figure 2:
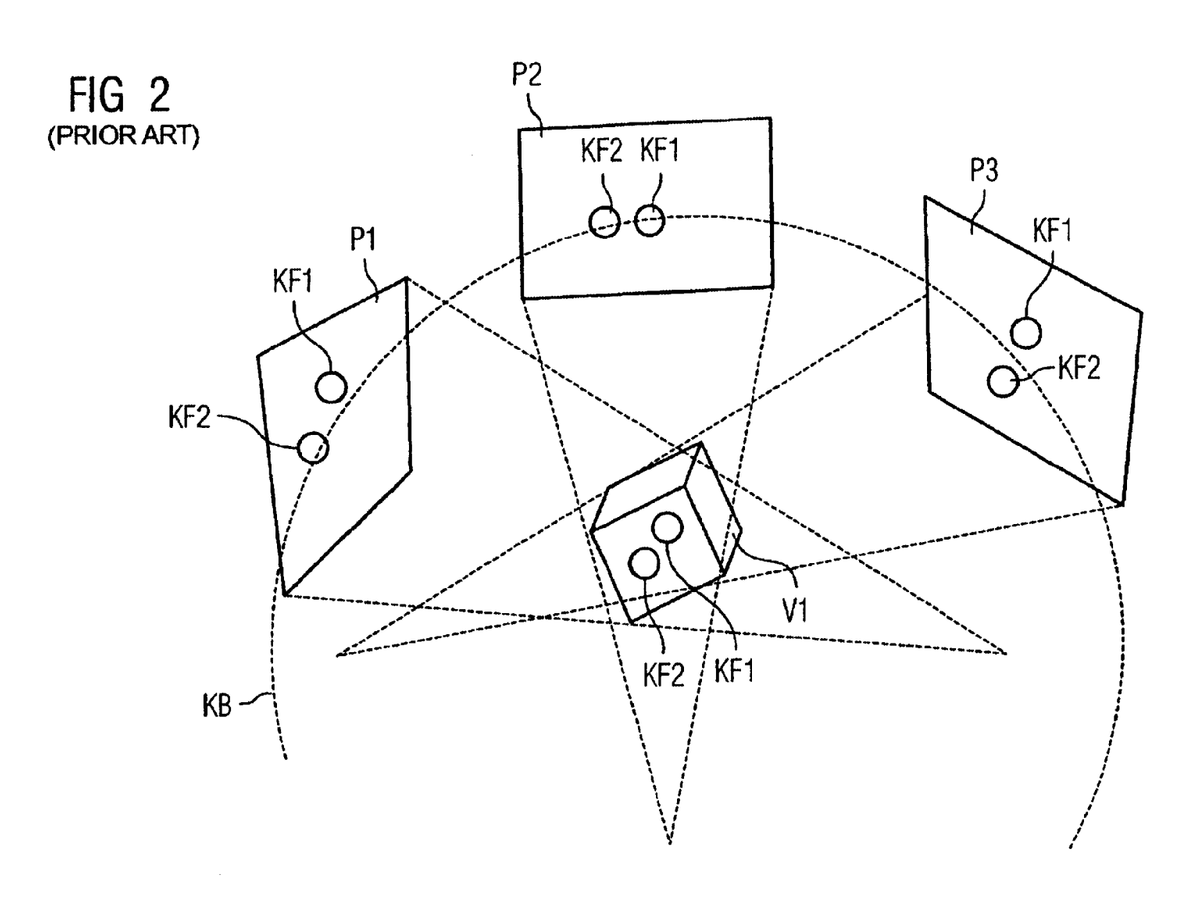
FIG. 2 schematically illustrates the reconstruction of a volume data set from a series of n 2D x-ray projections.

In the exemplary embodiment, a series of n 2D x-ray projections is acquired with the C-arm x-ray device 1 of the knee region K of the patient P (who has sustained a multiple fracture in the knee region K) at n different projection angles after the positioning of the patient P on the patient bed 11, by moving the C-arm 8, together with the x-ray source 9 and the x-ray radiation receiver 10 around its orbital axis A through approximately 190°. In the image computer 12, a voxel volume of the knee region K of the patient P is reconstructed by back-projection from the series of n 2D x-ray projections and the projection geometries that were determined for this adjustment movement of the C-arm 8 and stored. In schematic depiction, FIG. 2 illustrates the acquisition of the n 2D x-ray projections by movement of the C-arm 8 on an orbit KB, as well as the back-projection to reconstruct the voxel volume V1. The exemplary 2D x-ray projections P1 through P3 shown in FIG. 2, as well as the reconstructed voxel volume V1, each contain two points which should show images KF1 and KF2 of bone fragments. While the depiction of the images KF1 and KF2 of the bone fragments is two-dimensional in the 2D x-ray projections, their representation in the voxel volume V1 is three-dimensional (in a manner that cannot be recognized from FIG. 2).

From this voxel volume V1, which is present in the image computer 12, 3D images or 2D images of the knee region K can be generated by a known method (for example the MPR method (mulitplanar reformation)) and are shown on a display device 13 connected (in a manner not shown) with the image computer 12. For example, an image approximating the real-time appearance (generated from the first voxel volume V1) of the multiple fracture in the knee region K of the patient P is shown. In this manner, a surgeon (not shown in FIG. 1) treating the patient P can obtain an impression of the multiple fracture in the knee region K of the patient P and plan the osteosynthesis, i.e. the repositioning of the individual bone fragments KF and their subsequent setting.

In order to graphically show in the repositioning bone fragments changed with regard to their position and orientation relative to the initial positions shown in FIG. 2, and thus to be able to aid the surgeon in the osteosynthesis, the 3D images of the bone fragments (in the exemplary embodiment, the images KF1 and KF2) are segmented in the reconstructed voxel volume V1 such that the 3D contour of each bone fragment to be repositioned is identified in a visually recognizable manner. After position changes undertaken intraoperatively on the bone fragments, intraoperative m<n (for example m=5) 2D x-ray projections of the knee region K, and thus of the bone fragments of the patient P, are acquired at m different projection angles. For this purpose, the C-arm 8 is brought into the corresponding selected positions relative to the patient P. In the intraoperative acquisitions of the m 2D x-ray projections of the knee region K of the patient P, the C-arm 8 preferably occupy positions which substantially correspond to positions from which the 2D x-ray projections of the series of n 2D x-ray projections were already acquired. The 2D contours of the imaged bone fragments, changed with respect to their position, are segmented in the intraoperatively acquired m 2D x-ray projections. These 2D contours segmented in the intraoperatively acquired m 2D x-ray projections are, based on the determined projection geometries, back-projected in the image computer 12 in the reconstructed voxel volume V1, so that an updated voxel volume is produced that contains the 3D contours of the bone fragments in their initial position and the 3D contours of the bone fragments after their position change.

Figure 3:
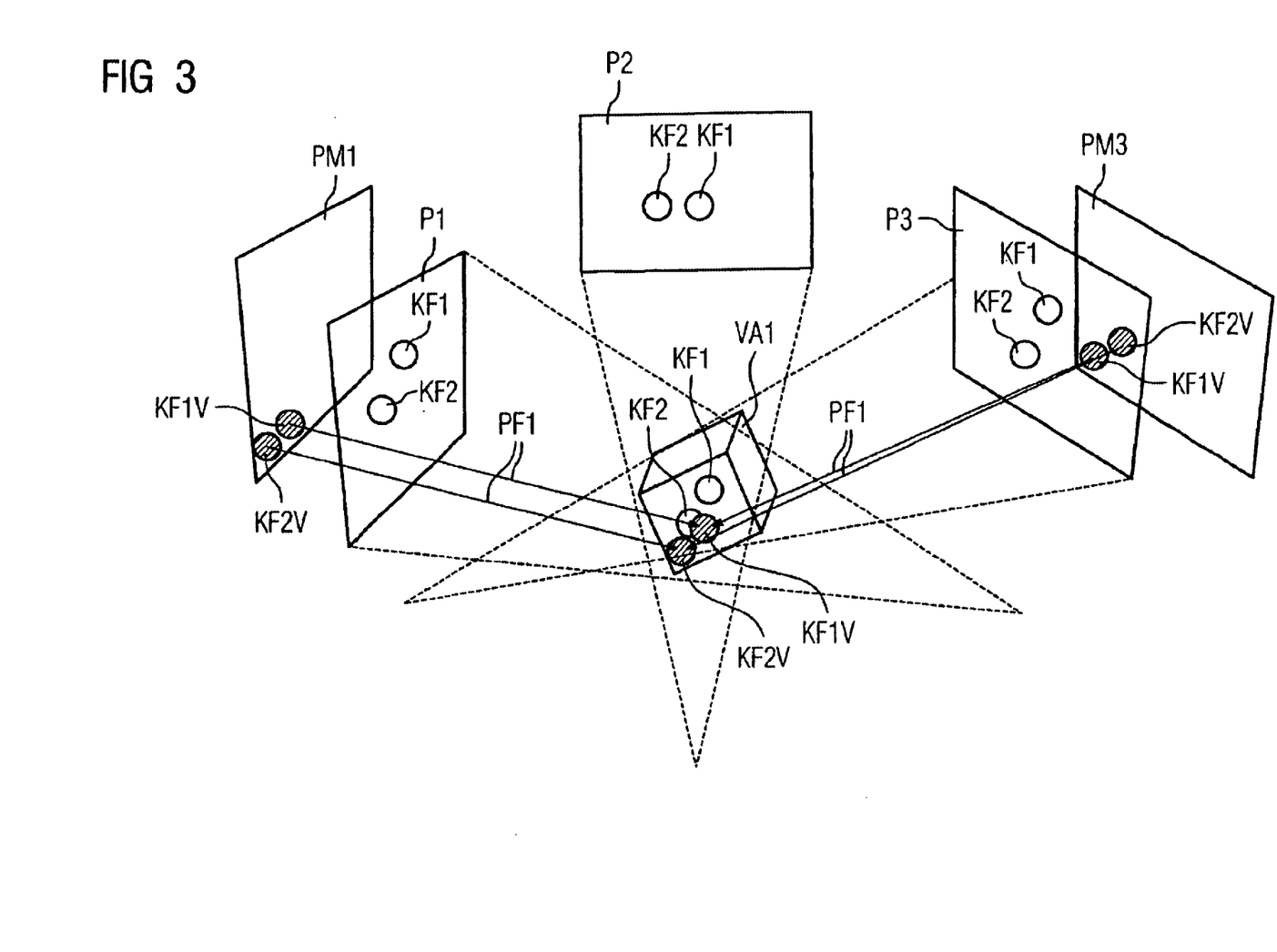
FIGS. 3 and 4 schematically illustrate the generation of an updated volume data set using m intraoperative acquired 2D x-ray projections in accordance with the invention.

The procedure is schematically illustrated in FIG. 3. As shown in FIG. 3, the 2D x-ray projection PM1 is intraoperatively acquired in the position of the C-arm 8 in which the 2D x-ray projection P1 was acquired, and the 2D x-ray projection PM3 is acquired in the position of the C-arm 9 in which the 2D x-ray projection P3 was acquired. The images KF1V and KF2V of the bone fragments (present in the 2D x-ray projections PM1 and PM3) which show their updated changed position are segmented in the 2d x-ray projections PM1 and PM3 such that each 2D contour is identified in a visually recognizable way allowing them to be differentiated. The segmented 2D contours of the images KF1V and KF2V of the bone fragments are then (as indicated with arrows PF1 in FIG. 3) back-projected in the reconstructed voxel volume V1, such that the updated voxel volume VA1 shown in FIG. 3 is obtained around the 3D contours of the images KF1V and KF2V of the bone fragments present in the 2D x-ray projections PM1 and PM3. The ensuing updated voxel volume VA1 subsequently contains, as is shown in FIG. 3, both 3D contours of the bone fragments in their initial position and orientation and, as an overlay, 3D contours of the bone fragments in their current position and orientation during the medical procedure. The 3D contours of the bone fragments in their changed position represented in the updated voxel volume VA1, which result from the few (for example m=5) intraoperatively acquired 2D x-ray projections, show the bone fragments shown in their initial position, as pseudo 3D contours. The imaging is sufficient, however to effectively aid the surgeon performing the procedure in the repositioning of the bone fragments.

In order, in the updated voxel volume VA1, to facilitate better differentiation of the 3D contours of the bone fragments in their initial position from the 3D contours of the bone fragments after their repositioning relative to one another, these contours preferably are grey or color coded. In the modified updated voxel volume, the 3D contours of the bone fragments in their original position and orientation are then, for example, grey coded, and the 3D contours of the bone fragments in their current position and orientation are shown color coded during the procedure.

In a second version of the inventive method, after the acquisition of the series of n 2D x-ray projections, and after the reconstruction of the ceramic component V1 shown in FIG. 2, the 3D contours of the bone fragments imaged in the voxel volume V1 are likewise segmented. Furthermore, after a position change of the bone fragments during the medical procedure, m 2D x-ray projections of the knee region K, and thus of the bone fragments of the patient P changed with regard to their position, are intraoperatively acquired at m different projection angles, and the 2D contours of the imaged bone fragments are segmented in the acquired m 2D x-ray projections. As previously described, in the acquisition of the m 2D x-ray projections the C-arm 8 is preferably brought to positions relative to the patient P at which 2D x-ray projections of the series of n 2D x-ray projections were already acquired, such that the projection geometries for the m 2D x-ray projections are known.

Based on the projection geometries for the m 2D x-ray projections, the 3D contours of the bone fragments segmented in the voxel volume V1 are subsequently projected as 2D contours in each of the m 2D x-ray projections in the image computer 12. In the reconstructed voxel volume, the 3D contours of the bone fragments are then virtually repositioned by rotational and/or translational adjustments in simultaneous projection in the m 2D x-ray projections until the 3D contours of the bone fragments projected in the m 2D x-ray projections are substantially congruent with the corresponding intraoperatively acquired 2D contours of the bone fragments in the m 2D x-ray projections. As used herein, "congruent" means that all corresponding points of corresponding 2D contours exhibit (according to a specified criterion) a sufficiently small separation from one another. Based on information acquired from this virtual repositioning, the voxel volume V1 is updated around 3D contours of the bone fragments illustrating the position change of the bone fragments, such that the 3D contours of the bone fragments in their initial position and the 3D contours of the bone fragments in their changed position are contained (represented) in the updated voxel volume.

Figure 4:
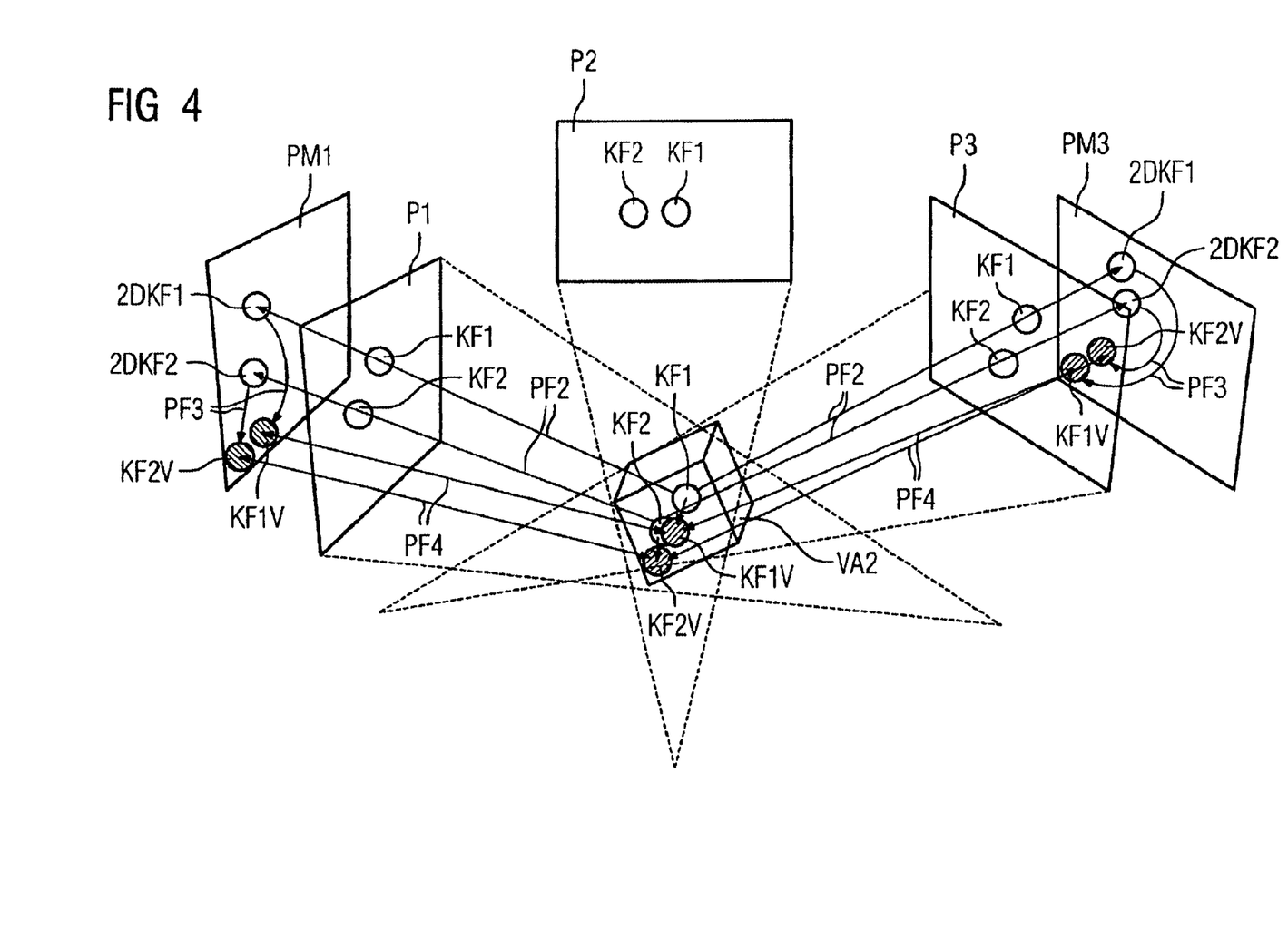

The principle of the two versions to intraoperatively update a volume data set is illustrated in FIG. 4. In the voxel volume V1 (reconstructed from, among other things, the 2D x-ray projections P1 through P3), in which the 3D contours of the images KF1 and KF2 of the bone fragments were segmented, the 3D contours of the images KF1 and KF2 are virtually repositioned until their 2D projections 2D KF1, 2D KF2 (indicated via arrows PF2) in the intraoperatively acquired 2D x-ray projections PM1 and PM3 are congruent with the images KF1V and KF2V of the bone fragments (which are segmented as 2D contours) exhibited in the intraoperatively acquired 2D x-ray projections PM1 and PM3. In FIG. 4, the displacement of the 2D projections 2D KF1, 2D KF2 of the 3D contours of the bone fragments is illustrated with arrows PF3 on the bone fragments imaged and segmented as a 2D contour in the intraoperatively acquired 2D x-ray projections PM1 and PM3. The displacement of the 2D projections 2D KF1, 2D KF2 in the 2D x-ray projections PM1, PM3 thereby results in adjustments of the 3D contours undertaken in the voxel volume V1 which are projected preferably continuously, correspondingly in the intraoperatively acquired 2D x-ray projections PM1 and PM3. The voxel volume VA2 shown in the FIG. 4 presents the final condition when, as is illustrated by the arrow PF4, congruity is achieved. The voxel volume VA2 then comprises, like the voxel volume VA1, 3D contours of bone fragments in their initial position and 3D contour of bone fragments after their repositioning.

In the second version, for the exemplary embodiment can be represented by the following structured chart:
For all of the m 2D x-ray projections:
  For all of the k bone fragments:
    Projection of the 3D contour of the bone fragments on the 2D x-ray projections.
    Is the separation between projected 3D contour and 2D contour sufficiently small?
      Yes→voxel volume is already current. No virtual repositioning of the bone fragment necessary→next bone fragment
    For all degrees of rotation/translation/freedom of the bone fragments:
      Change of the degrees of freedom
        Is the separation between projected 3D contour and 2D contour sufficiently small?
          Yes→voxel volume is already current. No virtual repositioning of the bone fragment necessary→next bone fragment In the second version, in order to be better able to differentiate the 3D contours of the bone fragments in their initial position from the 3D contours of the bone fragments after their repositioning from one another in the updated voxel volume VA2, these are preferably shown coded. In this manner, a modified updated voxel volume is achieved in which the image information of the bone fragments in their original position and orientation is shown (for example) grey coded, and the image information of the bone fragments in their current position and orientation during the procedure is shown color coded.

As previously mentioned for both versions, it is proven to be advantageous when, in an intraoperative acquisition of one of the m 2D x-ray projections, the C-arm 8 occupies a position relative to the patient P that is substantially the same as in the acquisition of a 2D x-ray projection of the series of n 2D x-ray projections, since in this case for the m 2D x-ray projection the projection geometries necessary for the backprojection are known. The movement to such an position can be achieved, for example, by automatically moving the C-arm 8 to such a position via an input from an operator console 15 indicated in FIG. 1, provided with an input means. In FIG. 1, an electromotor 16 controllable from the operator console 15 is shown for the orbital adjustment of the C-arm 8 along its perimeter in the positioner 7. Via a corresponding procedure at the operator console 15, the C-arm 8 can be subsequently automatically moved in each position that the C-arm 8 had occupied in the acquisition of any of the n 2D x-ray projections of the knee region K of the patient P. For the adjustment of the C-arm 8 around its angulation axis B, a corresponding electromotor (which is not shown in the FIG. 1) is provided that is also controllable from the operator console 15.

Movement of the C-arm 8 to a position in the intraoperative acquisition of a 2D x-ray projection, which corresponds to a position of the C-arm 8 in the acquisition of a 2D x-ray projection of the series of n 2D x-ray projections, alternatively can be achieved such that the C-arm 8 is manually adjusted by means of a handle shown in the FIG. 1, which ensues under the supervision of angle or position transmitters which are provided in FIG. 1 with the reference numbers 18 and 19.

In the intraoperative acquisition of one of the m 2D x-ray projections, a third possibility to bring the C-arm 8 into a position that the C-arm 8 had already occupied in the acquisition of a 2D x-ray projection of the series of n 2D x-ray projections is the use of a mechanical arresting device. In the exemplary embodiment, the mechanical arresting device has five bores 20 through 24 introduced into the C-arm 8 and a hook-shaped device 25 arranged at the positioner 7 which can be inserted into any one of the openings 20 through 24 to arrest the C-arm 8. In the exemplary embodiment, the hook-shaped device 25 is inserted into the opening 21 and thus arrests the C-arm 8 in a defined position which corresponds to a position that the C-arm 8 had previously occupied in the acquisition of a 2D x-ray projection of the series of n 2D projections.

It is of course possible in the intraoperative acquisition of 2D x-ray projections, for the C-arm 8 to occupy positions relative to the patient P, or the knee region K of the patient P, other than those occupied in the acquisition of the 2D x-ray projections of the series of n 2D x-ray projections. In this case, however, the projection geometries for these positions of the C-arm 8 must either be determined in a separate calibration process before the actual patient measurement, for example with the x-ray calibration phantom specified in German OS 100 47 382, or the projection geometries are calculated for the C-arm 8 at these positions by the image computer 12 by means of interpolation of the already known or determined projection geometries.

Insofar as the projection geometries are known for these positions of the C-arm 8, in the case of the first version of the inventive method the 2D contours, segmented in the m 2D x-ray projections, are back-projected in the voxel volume in a known manner using these projection geometries.

In the case of the second version of the inventive method, after the determination of the projection geometries the 3D contours are projected from the voxel volume as 2D contours in the m 2D x-ray projections in a known manner with the image computer 12 and brought into congruence with the 2D contours of the bone fragments imaged in the intraoperatively acquired m 2D x-ray projections.

The versions of inventive method have been explained in the example of a movable C-arm x-ray device. The method can be implemented not only with movable C-arm x-ray devices, but also with stationary C-arm x-ray devices or other x-ray devices with which the generation of a volume data set is possible from 2D x-ray projections.

Furthermore, the inventive method was explained in the context of the repositioning of bone fragments. However, the method is not only applicable to the repositioning of bone fragments, can be used with volume data sets of other types of biological tissue, or even other objects within the body of a patient, to update images after position changes of the biological tissue or the object.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for intraoperatively generating and updating a volume dataset, comprising the steps of:
   (a) acquiring a series of n 2D x-ray projections of biological tissue, in an initial position, of a patient respectively at n different projection angles with an x-ray system, each of said projections having an associated projection geometry selected from the group consisting of known projection geometries and determinable projection geometries, said n 2D x-ray projections forming a volume dataset for said biological tissue;
   (b) reconstructing image information of said volume dataset representing said biological tissue from said n 2D x-ray projections using said associated projection geometries;
   (c) after a positional change of said biological tissue, intraoperatively acquiring a series of m 2D x-ray projections of said biological tissue respectively at m different projection angles with said x-ray system, wherein m <n, said m 2D x-ray projections forming a further volume dataset;
   (d) for each of said intraoperatively acquired m 2D x-ray projections, obtaining an associated projection geometry;
   (e) segmenting image information of said further volume dataset so that a 2D contour of the biological tissue is present in each of said m 2D x-ray projections; and
   (f) using the respective projection geometries obtained in step (d) back-projecting said 2D contours that are segmented in the respective m 2D x-ray projections into the image information of said volume dataset reconstructed in step (d), to produce an updated volume dataset containing a 3D contour of said biological tissue after said position change.

2. A method as claimed in claim 1 wherein said updated volume dataset comprises a 3D contour of said biological tissue in said initial position and a 3D contour of said biological tissue after said positional change, respectively displayed in a visually coded manner allowing visual differentiation of the respective 3D contours.

3. A method as claimed in claim 2 comprising displaying the respective 3D contours with coding selected from the group consisting of grey scale coding and color coding.

4. A method as claimed in claim 1 wherein steps (a) and (c) comprise acquiring said series of n 2D x-ray projections and said series of m 2D x-ray projections of bone fragments, as said biological tissue.

5. A method as claimed in claim 1 comprising positioning said x-ray system in step (c) for acquiring said series of m 2D x-ray projections at respective positions that are substantially the same as respective positions of said x-ray system for acquiring said series of n 2D x-ray projections in step (a).

6. A method as claimed in claim 5 comprising automatically bringing said x-ray system to said same positions by a motor drive of said x-ray system.

7. A method as claimed in claim 5 comprising manually bringing said x-ray system to said same positions with electronic monitoring from at least one of angle transmitters and position transmitters.

8. A method as claimed in claim 5 comprising bringing said x-ray system to said same positions using a mechanical arresting mechanism that interacts with said x-ray system.

9. A method as claimed in claim 1 comprising positioning said x-ray system in step (c) for obtaining said m 2D x-ray projections at positions that are respectively different from positions of said x-ray system in step (a) for acquiring said series of n 2D x-ray projections, and wherein step (d) comprises obtaining said projection geometries respectively associated with said m 2D x-ray projections by calculation, in a calibration procedure, from said projection geometries in step (a).

10. A method as claimed in claim 1 comprising positioning said x-ray system in step (c) for obtaining said m 2D x-ray projections at positions that are respectively different from positions of said x-ray system in step (a) for acquiring said series of n 2D x-ray projections, and wherein step (d) comprises obtaining said projection geometries respectively associated with said m 2D x-ray projections by interpolation, from said projection geometries in step (a).

11. A method as claimed in claim 1 comprising employing a C-arm x-ray apparatus, having an x-ray source and a radiation receiver mounted on a C-arm, as said x-ray system in steps (a) and (c).

12. A method for intraoperatively generating and updating a volume dataset, comprising the steps of:
   (a) acquiring a series of n 2D x-ray projections of biological tissue, in an initial position, of a patient respectively at n different projection angles with an x-ray system, each of said projections having an associated projection geometry selected from the group consisting of known projection geometries and determinable projection geometries, said n 2D x-ray projections forming a volume dataset for said biological tissue;
   (b) reconstructing image information of said volume dataset representing said biological tissue from said n 2D x-ray projections using said associated projection geometries;
   (c) segmenting image information in said volume dataset of said biological tissue to produce a 3D contour of said biological tissue in said volume dataset;
   (d) after a positional change of said biological tissue, intraoperatively acquiring a series of m 2D x-ray projections of said biological tissue respectively at m different projection angles with said x-ray system, wherein m<n, said m 2D x-ray projections forming a further volume dataset;

(e) for each of said intraoperatively acquired m 2D x-ray projections, obtaining an associated projection geometry;

(f) projecting said 3D contour of said biological tissue that was segmented in step (c) in said volume dataset into each of said m 2D x-ray projections acquired in step (d);

(g) repositioning the 3D contour of the biological tissue that is segmented in aid volume dataset until said 3D contour projected into each of said end 2D x-ray projections is substantially congruent with image information of said biological tissue in the respective m 2D x-ray projections; and (h) supplementing said volume dataset with a further 3D contour visually representing said position change of said biological tissue, to produce an updated volume dataset.

13. A method as claimed in claim 12 wherein step (g) comprises repositioning said 3D contour by an adjustment selected from the group consisting of rotational adjustments and translational adjustments until said substantial congruity is achieved.

14. A method as claimed in claim 12 wherein said updated volume dataset comprises a 3D contour of said biological tissue in said initial position and a 3D contour of said biological tissue after said positional change, respectively displayed in a visually coded manner allowing visual differentiation of the respective 3D contours.

15. A method as claimed in claim 14 comprising displaying the respective 3D contours with coding selected from the group consisting of grey scale coding and color coding.

16. A method as claimed in claim 12 wherein steps (a) and (d) comprise acquiring said series of n 2D x-ray projections and said series of m 2D x-ray projections of bone fragments, as said biological tissue.

17. A method as claimed in claim 12 comprising positioning said x-ray system in step (d) for acquiring said series of m 2D x-ray projections at respective positions that are substantially the same as respective positions of said x-ray system for acquiring said series of n 2D x-ray projections in step (a).

18. A method as claimed in claim 17 comprising automatically bringing said x-ray system to said same positions by a motor drive of said x-ray system.

19. A method as claimed in claim 17 comprising manually bringing said x-ray system to said same positions with electronic monitoring from at least one of angle transmitters and position transmitters.

20. A method as claimed in claim 17 comprising bringing said x-ray system to said same positions using a mechanical arresting mechanism that interacts with said x-ray system.

21. A method as claimed in claim 12 comprising positioning said x-ray system in step (d) for obtaining said m 2D x-ray projections at positions that are respectively different from positions of said x-ray system in step (a) for acquiring said series of n 2D x-ray projections, and wherein step (e) comprises obtaining said projection geometries respectively associated with said m 2D x-ray projections by calculation, in a calibration procedure, from said projection geometries in step (a).

22. A method as claimed in claim 12 comprising positioning said x-ray system in step (d) for obtaining said m 2D x-ray projections at positions that are respectively different from positions of said x-ray system in step (a) for acquiring said series of n 2D x-ray projections, and wherein step (e) comprises obtaining said projection geometries respectively associated with said m 2D x-ray projections by interpolation, from said projection geometries in step (a).

* * * * *